US00PP32356P3

(12) United States Plant Patent
Kurabayashi

(10) Patent No.: US PP32,356 P3
(45) Date of Patent: Oct. 20, 2020

(54) ***RHODODENDRON* PLANT NAMED 'TRITON'**

(50) Latin Name: ***Rhododendron* hybrid**
Varietal Denomination: Triton

(71) Applicant: Kabushiki Gaisha Akatsuka Garden Co., Ltd., Tsu-shi, Mie-ken (JP)

(72) Inventor: Yukio Kurabayashi, Tsu (JP)

(73) Assignee: KABUSHIKI GAISHA AKATSUKA GARDEN CO., LTD., Tsu-Shi, Mie-Ken (JP)

( * ) Notice: Subject to any disclaimer, the term of this patent is extended or adjusted under 35 U.S.C. 154(b) by 0 days.

(21) Appl. No.: 16/501,340

(22) Filed: Mar. 28, 2019

(65) Prior Publication Data

US 2019/0394916 P1 Dec. 26, 2019

(30) Foreign Application Priority Data

Jun. 20, 2018 (JP) ..... PBR 33200

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238, 239, 240
CPC ..... A01H 5/02; A01H 5/00
See application file for complete search history.

*Primary Examiner* — Kent L Bell
(74) *Attorney, Agent, or Firm* — Cantor Colburn LLP

(57) ABSTRACT

The present invention relates to a new and distinct variety of plant named 'Triton'. The variety is botanically identified as *Rhododendron* hybrid. The new variety is distinguished from other varieties by a number of properties, including but not limited to, corolla lobe color.

5 Drawing Sheets

Latin name of the plant claimed: The variety is botanically identified as *Rhododendron* hybrid.

CROSS-REFERENCE TO RELATED APPLICATION

This application claims benefit of Japanese Plant Variety Protection Application No. 33200, filed on Jun. 20, 2018, which is incorporated herein in its entirety.

BACKGROUND OF THE INVENTION

The new variety 'Triton' originated from the controlled cross of the plants 'Stardust' and 'Pink Ice' performed in April 2012 in Anoucho, Tsu-shi, Mie-ken, Japan. In 2015, the new variety having early blooming, attractive rimmed flowers was discovered and selected by the Inventor as a single flowering plant within the progeny of the stated controlled cross-pollination in Anoucho, Tsu-shi, Mie-ken, Japan. As a result of tissue cultures from 2015 and trial production in the field, 'Triton' was determined as being an excellent variety with beautiful blooms in May 2018, and breeding was completed.

SUMMARY

The present invention relates to a new and distinct variety of plant named 'Triton'. The variety is botanically identified as *Rhododendron* hybrid. The new variety is distinguished from other varieties by a number of characteristics as set forth below.

When compared to the 'Mrs. Fujii' (not patented) variety having blossoms with a primary color that is pale pink, almost white (R.H.S. colour chart N74D) and a secondary color that is a very pale purple (R.H.S. colour chart 76D), the new variety of the present invention has been found to exhibit attractive blossoms with a principle deep purplish pink color (R.H.S. colour chart N74C) and a secondary color that is very pale purple (R.H.S. colour chart 76C). The annual blooming time for 'Triton' is about 10 days later than 'Mrs. Fujii'. 'Triton' has larger leaves (about 14 centimeters (cm) in length and about 6.0 cm in width) compared to 'Mrs. Fujii' (about 10 cm in length and about 2.5 cm in width). The branch color of a one-year old plant of 'Triton' is light brown (R.H.S. colour chart 173A), whereas the branch color of a one-year old plant of 'Mrs. Fujii' is dark red purple, almost brown (R.H.S. colour chart 180A). 'Triton' has a smaller truss size (about 18 cm in diameter and about 18 cm in height) than 'Mrs. Fujii' (25 cm in diameter and 20 cm in height). 'Triton' has more corolla per truss, about 20, than 'Mrs. Fujii', about 15, but the size of the corolla of 'Triton' is smaller (about 8 cm in length, about 8 cm in height, and about 6 cm in thickness) than 'Mrs. Fujii' (about 10 cm in length, about 10 cm in height, and about 5 cm in thickness).

'Triton' can be compared to its female parent 'Stardust' (not patented), and its male parent 'Pink Ice' (not patented). 'Stardust' has a height of about 80 cm and has spotted, light-purple flowers that bloom on April 20. 'Pink Ice' has a height of about 200 cm and pale pink flowers without spots that bloom on April 10. In contrast, 'Triton' has a height of about 40-50 cm and flowers with a principle deep purplish pink color (R.H.S. colour chart N74C) and a secondary color that is very pale purple (R.H.S. colour chart 76C), without spots, which bloom on April 1.

'Triton' can also be compared to its sibling cultivars, 'Kurachiffon' (U.S. patent application Ser. No. 16/501,342) and 'Kurachouchou' (U.S. patent application Ser. No. 15/501,341). 'Triton' blooms earlier than 'Kurachiffon', April 1 versus April 15, respectively. 'Triton' flowers have a principle deep purplish pink color (R.H.S. colour chart N74C), without spots, and 'Kurachiffon' flowers have a principle light reddish purple color (R.H.S. colour chart N75A), with weak spots (R.H.S. colour chart N74B). 'Triton' blooms earlier than 'Kurachouchou', April 1 versus May 5, respectively. 'Kurachouchou' flowers a principle color that is a strong purplish red (R.H.S. colour chart 71C) with weak spots (R.H.S. colour chart 71B), and 'Triton' flowers have a principle color that is dark purplish pink (R.H.S. colour chart N74C) without spots.

BRIEF DESCRIPTION OF THE DRAWINGS

The accompanying photographs show typical specimens of the new variety, including foliage and flowers, in color as nearly true as it is reasonably possible to make in color illustrations of these characteristics.

DESCRIPTION OF THE VARIETY

Figure 1:
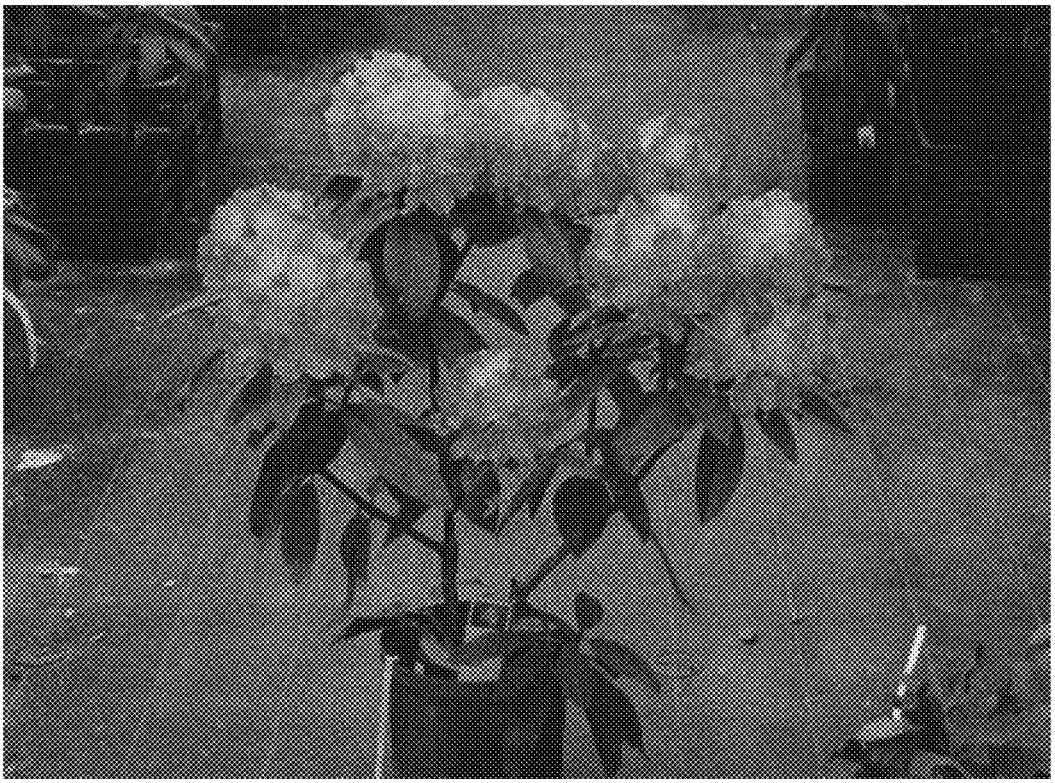
FIG. 1 illustrates the upper side of the flowers and the plant.
Figure 2:
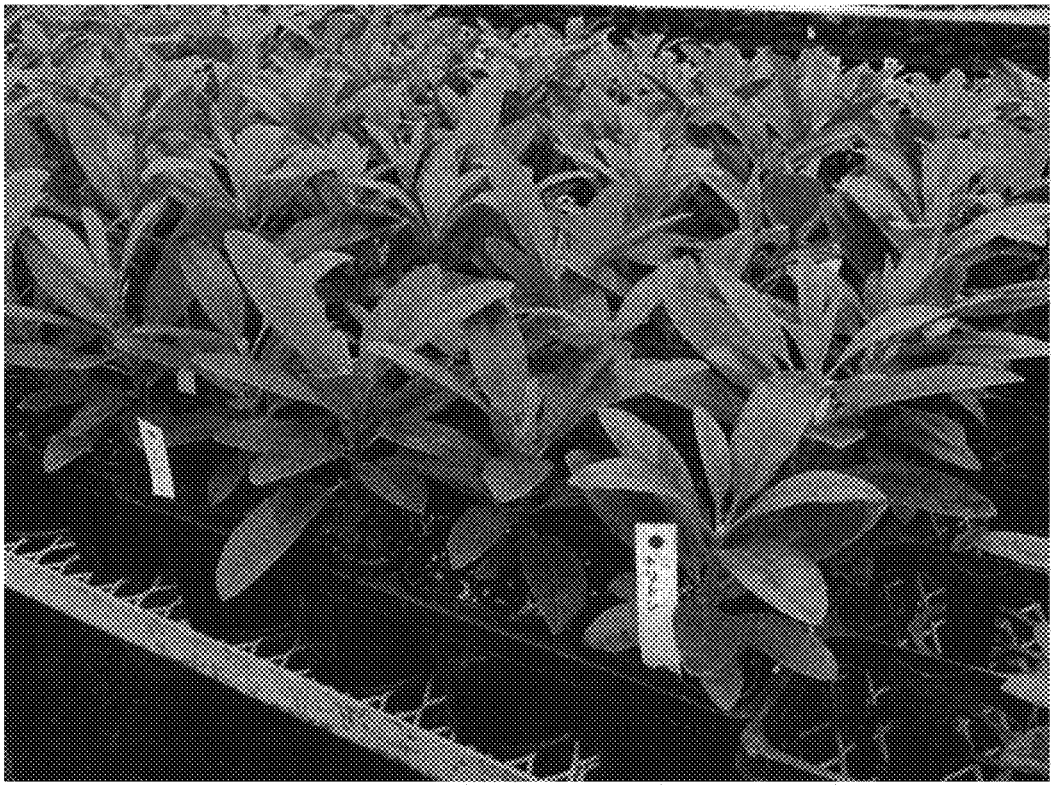
FIG. 2 illustrates a full view of the cultivation area showing the leaves of the plant.
Figure 3:
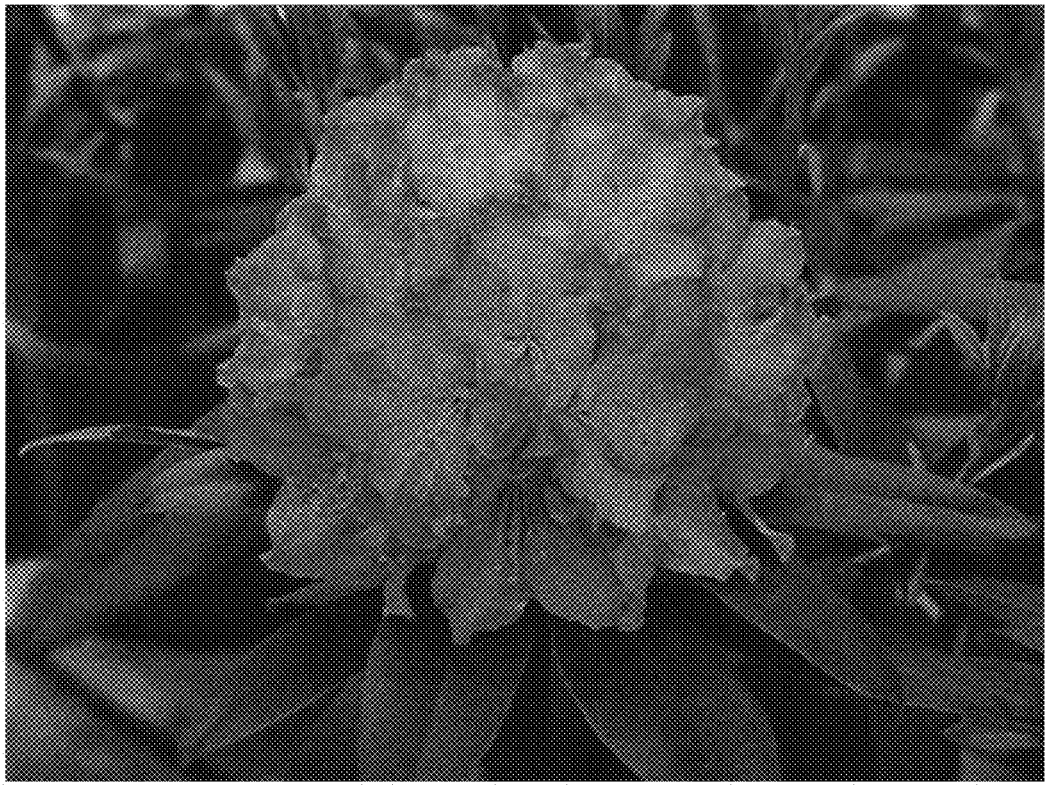
FIG. 3 illustrates a close-up of the flower.
Figure 4:
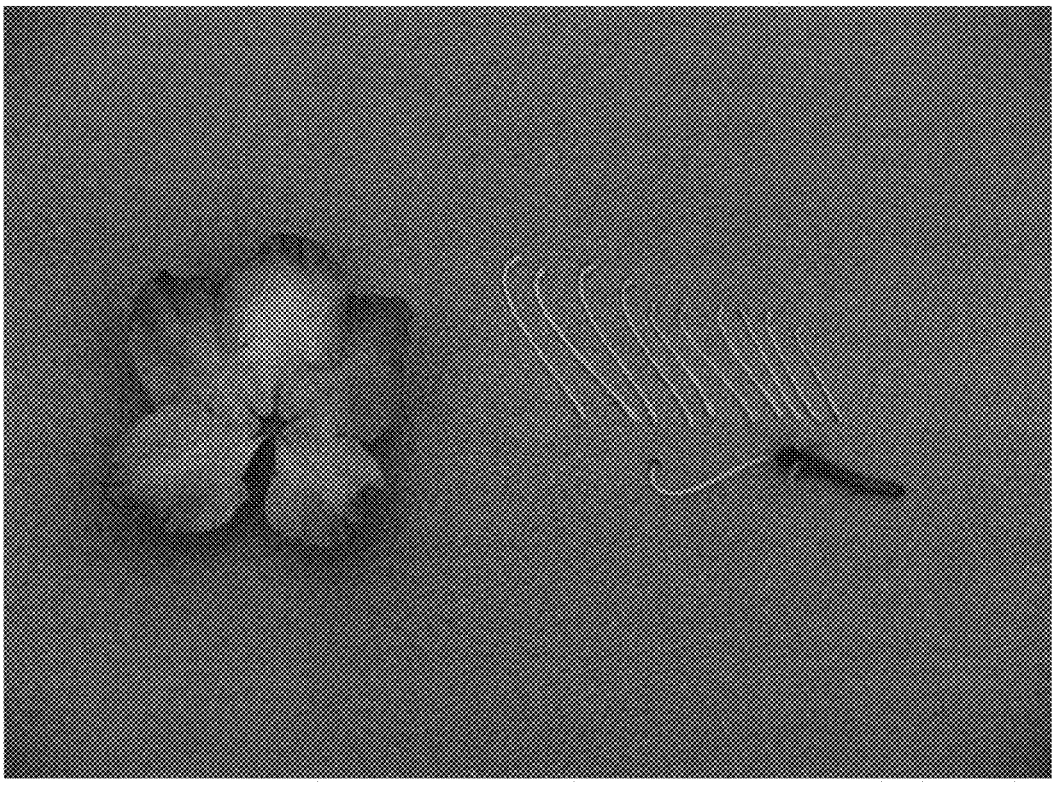
FIG. 4 illustrates a close-up of the dissected flower.
Figure 5:
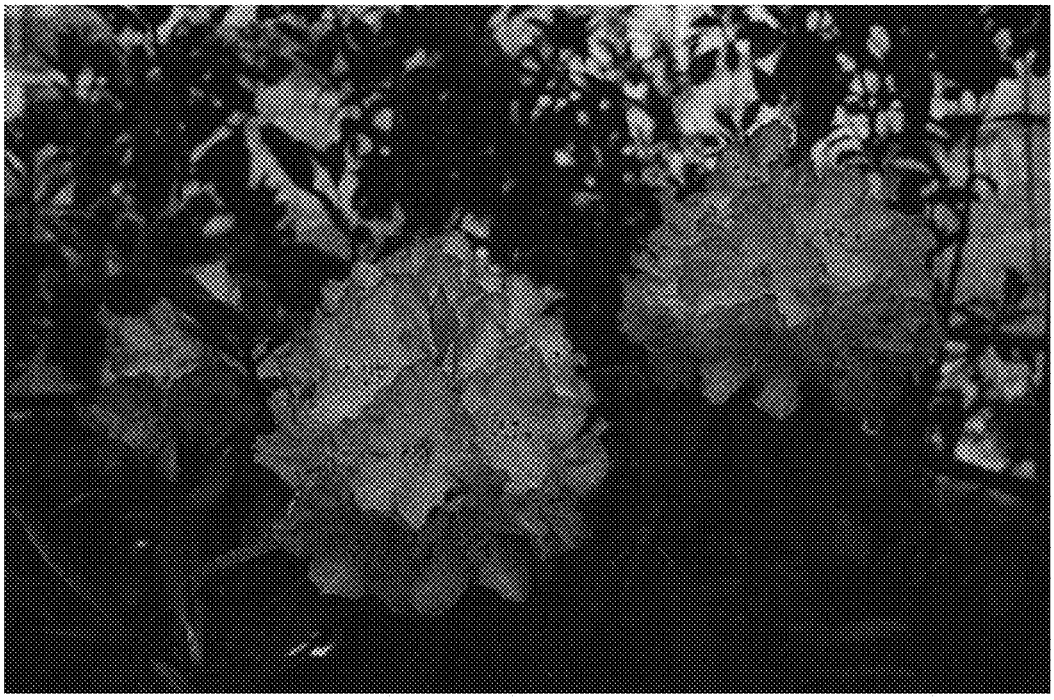
FIG. 5 illustrates, for comparison, the upper side of the flowers and the plant of 'Mrs. Fujii'.

The following detailed description of the new variety is based upon observations taken of plants grown in Anoucho, Tsu-shi, Mie-ken, Japan. Observations of 'Triton' were taken during the 2015 growing season.

In the following description, color references are made to The Royal Horticultural Society (R.H.S.) Colour Chart, except where general terms of ordinary dictionary significance are used.

Botanical classification: *Rhododendrum* hybrid.

Principle Use: Flowering shrub for potted plant and open-field cultivation.

Parentage: The female parent is 'Stardust', and the male parent 'Pink Ice'.

Propagation: The new variety was propagated using tissue cultures from plants potted in greenhouse facilities in Anoucho, Tsu-shi, Mie-ken, Japan. Growth points were collected from lateral buds of shoots, and cultivation and growth were performed without using calli.

Plant:

*Size*.—At 3 years of age, plants of the new variety commonly exhibit a height of about 40-50 cm and a width of about 30 cm.

*Habit*.—Vigorous and compact.

Foliage:

*Arrangement*.—Foliage arrangements are pseudoverticillate or false verticillate, appearing whorled or verticillate, but not actually so.

*Type*.—Evergreen flowering shrub, simple lanceolate leaves with an obtuse leaf base, oblong body, acute apex, and entire margins. The upper surfaces of the leaves appear semi-glossy, and the bottom surfaces of the leaves appear matte.

*Venation*.—Leaves have a netted (reticulate) venation pattern. R.H.S. colour chart 144C on the upper surface of the leaves, and R.H.S. colour chart 145D on the bottom surface.

*Size*.—Mature leaves growing midway up the stem commonly are approximately 14 cm in length and approximately 6 cm in width.

*Color*.—R.H.S. colour chart NN137A on the upper surface, and R.H.S. colour chart 143C on the under surface.

Petioles:

*Size*.—2.0 cm in length, and 3.0 millimeters (mm) in diameter.

*Texture*.—Rough with bristles.

*Color*.—R.H.S. colour chart 146C.

Branches:

*Size*.—Mature lateral branches (one-year old wood) are 1.5 meter (m) in length and 7.0 mm in diameter.

*Internode length*.—Mature lateral branches (one year old wood) have a 1.0 cm internode length.

*Texture*.—Mature lateral branches (one year old wood) are rough with bristles.

*Color*.—Mature lateral branches (one-year old wood) — R.H.S. colour chart 173A.

Peduncles:

*Size*.—Approximately 3.0 cm in length and 2.5 mm in diameter.

*Color*.—R.H.S. colour chart 137C.

Petals:

*Shape*.—Petals are generally wavy with a connected base and sharply pointed apex.

*Size*.—Approximately 6.0 cm in length and 3.5 cm in width.

*Texture*.—Both surfaces of the petals are generally smooth.

Sepals: None.

Flowers:

*Period*.—Blooms approximately April 1 in the evening when cultured at Anoucho, Tsu-shi, Mie-ken, Japan.

*Appearance*.—Corymb.

*Arrangement*.—Spheroidal.

*Truss shape*.—Generally a sphere.

*Truss size*.—Approximately 18 cm diameter, and approximately 18 cm in height.

*Corolla per truss*.—Approximately 20.

*Corolla shape*.—Open funnel shape.

*Corolla size*.—Approximately 8 cm in length, 8 cm in width, and 6 cm in thickness.

*Number of lobes*.—Five lobes per floret.

*Margin of lobes*.—Wavy to frilly.

*Fragrance*.—None.

*Calyx size*.—Approximately 2 millimeters (mm) in length.

*Flower bud shape*.—Lacrimoid.

*Flower bud size*.—Approximately 4.0 mm in length and 2.5 cm in diameter.

*Flower bud color*.—R.H.S. colour chart N74B. Flower color — Two colors on the surface of the corolla lobe, with the same color on both the upper and lower surfaces. The principle color on the surfaces of the corolla lobe is dark purplish pink (R.H.S. colour chart N74C). The secondary color on the surfaces of the corolla lobe is very pale purple (R.H.S. colour chart 76C). No spots are present on the throat of the corolla lobe.

*Longevity*.—10 days.

Reproductive organs:

*Stamen number*.—10.

*Filament length*.—Approximately 4.9 cm.

*Filament color*.—R.H.S. colour chart 76D.
*Anther shape*.—Barrel shaped.
*Anther length*.—Approximately 2.0 mm.
*Anther color*.—R.H.S. colour chart 155A.
*Pollen amount and color*.—High pollen count and R.H.S. colour chart 155A.
*Pistil length*.—Approximately 3.5 cm.
*Stigma shape*.—Captiform.
*Stigma color*.—R.H.S. colour chart 186A.
*Style length*.—Approximately 3.0 cm.
*Style color*.—R.H.S. colour chart 157D.
*Ovary color*.—R.H.S. colour chart 35A.

Winter hardiness: Has survived winters with temperatures as low as −3° C. in Anoucho, Tsu-shi, Mie-ken, Japan.
Disease resistance: During observations to date, the foliage has been disease resistant. Although generally, *Rhododendron* hybrid plants are prone to root rot disease, which tends to occur in high temperatures, 'Triton' is resistant to root rot because it is resistant to high temperatures.
Successive generations: Reproduces true to type in successive generations as set forth above.

What is claimed is:

1. A new and distinct variety of *Rhododendron* hybrid plant, substantially as shown and described.

* * * * *